US00PP09036P

United States Patent [19]

Meier et al.

[11] Patent Number: Plant 9,036

[45] Date of Patent: Jan. 3, 1995

[54] BA 73-366 KENTUCKY BLUEGRASS

[75] Inventors: Virgil D. Meier, Marysville, Ohio; J. Kevin Turner, South Salem, Oreg.; Eugene W. Mayer, Marysville, Ohio

[73] Assignee: The O. M. Scott and Sons Company, Marysville, Ohio

[21] Appl. No.: 125,564

[22] Filed: Sep. 23, 1993

[51] Int. Cl.[6] ..... A01H 5/00

[52] U.S. Cl. ..... Plt./90.2

[58] Field of Search ..... Plt. 90.2

[56] References Cited

U.S. PATENT DOCUMENTS

| | | | |
|---|---|---|---|
| PP3156 | 5/1972 | Fuchigami et al. | Plt./90.2 |
| PP3186 | 5/1972 | Barenbrug et al. | Plt./90.2 |
| PP4336 | 11/1978 | Mayer et al. | Plt./90.2 |
| PP6280 | 9/1988 | Meier et al. | Plt./90.2 |
| PP6537 | 1/1989 | Meier et al. | Plt./90.2 |
| PP6538 | 1/1989 | Meier et al. | Plt./90.2 |
| PP6585 | 2/1989 | Meier et al. | Plt./90.2 |
| PP7831 | 3/1992 | Meier et al. | Plt./90.2 |
| PP8490 | 12/1993 | Meier et al. | Plt./90.2 |

*Primary Examiner*—James R. Feyrer

[57] ABSTRACT

A variety of Kentucky bluegrass having a medium to high level of disease resistance, a desirable green color throughout the growing season, good drought recovery capability, a medium to high quality dense presistent turf forming ability under a wide variety of environmental conditions, and a high level of seed yielding capacity.

3 Drawing Sheets

BACKGROUND

Kentucky bluegrasses have been disclosed in U.S. Plant Pat. No. 3,156 which issued on May 9, 1972; U.S. Plant Pat. No. 3,186 which issued on May 23, 1972; U.S. Plant Pat. No. 4,336 which issued on Nov. 28, 1978; U.S. Plant Pat. No. 6,280 which issued on Sep. 6, 1988; U.S. Plant Pat. No. 6,537 which issued on Jan. 17, 1989; U.S. Plant Pat. No. 6,538 which issued on Jan. 17, 1989 and U.S. Plant Pat. No. 6,585 which issued on Feb. 7, 1989; U.S. Plant Pat. No. 7,831 which issued on Mar. 17, 1992 and U.S. Plant patent application Ser. No. 07/821,403 which was filed on Jan. 14, 1992, now U.S. Plant Pat. No. 8,490.

SUMMARY OF THE VARIETY

The present invention relates to a new and improved variety of Kentucky bluegrass, *Poa pratensis*, that has been designated Ba 73-366.

Ba 73-366 plant material originated as a single plant selection from the open pollinated progeny of a Kentucky bluegrass seed parent developed and maintained in the O. M. Scott plant nursery at Marysville, Ohio. This seed parent was identified as Ba 65-125 in the O. M. Scott breeding program. At the time of selection, the Ba 73-366 plant appeared different from other progency plants which originated from apomictically produced seeds of Ba 65-125. As a result of this selection, a distinct variety was produced and asexually propagated by rhizomes, tillers and disseminules. Seed of Ba 73-366 was produced first at Marysville, Ohio and later at Gervais, Ore. This seed was used to plant turf performance evaluation trials and later seed production fields.

Asexual production of Ba 73-366 by propagules (tillers and rhizomes) and by disseminules (modified caryopses produced by apomixis) has consistently produced progeny plants indistinguishable from the mother plant. The apomixis level of Ba 73-366 is approximately 99% based upon examining seedling characteristics of approximately 100 to 150 seedlings from five different crop years in a growth chamber.

Ba 73-366 has a number of highly desirable characteristics including a medium to high level of resistance to Dreschslera spp. (formerly called Helminthosporium spp.) that causes leaf spot, melting out and crown rot; Puccinia spp. that causes several types of rust infections; and *Sclerotinia homoeocarpa* that causes dollar spot. Ba 73-366 has an attractive leafy turf type growth habit; moderately wide leaf blades; attractive green color which can be maintained throughout the entire growing season; good drought recovery capability and good turf performance as evidenced by consistently good to high scores for quality, color and density. Ba 73-366 has a high seed yield potential in the bluegrass seed production region of northwestern U.S.A.

In comparison with a number of other Kentucky bluegrasses, Ba 73-366 differs significantly in regard to the following morphological characteristics: (1) length and width of panicle, (2) whorls per panicle, (3) branches per whorl and (4) number of florets per spikelet.

Ba 73-366 has average size spikelets and glumes, flag leaf of average length but broader in width and a tendency towards a thinner leaf. Ba 73-366 has a statistically significant large flag leaf ligule and a lower level of sheath color than most other Kentucky bluegrasses tested.

Ba 73-366 has a long peduncle, average peduncle width, a culm length significantly longer than a number of other bluegrasses and a high number of nodes per culm. Also, it has an average size vegetative leaf in length and width but a statistically significant thicker leaf and leaf margin hairs. Ba 73-366 has significantly more hairs on the back side of the ligule. Under close mowing as practiced under lawn maintenance conditions, Ba 73-366 has a broader leaf blade than a number of other Kentucky bluegrasses.

DETAILED DESCRIPTION OF THE VARIETY

Figure 1:
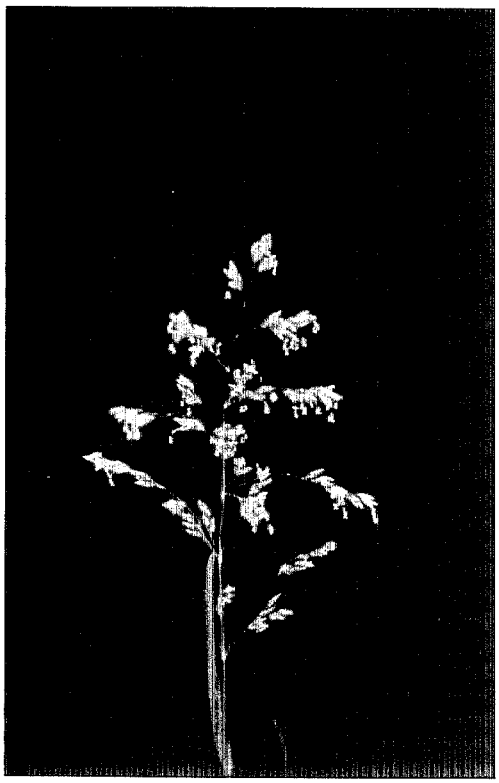
FIG. 1 is a Ba 73-366 Kentucky bluegrass panicle.
Figure 2:
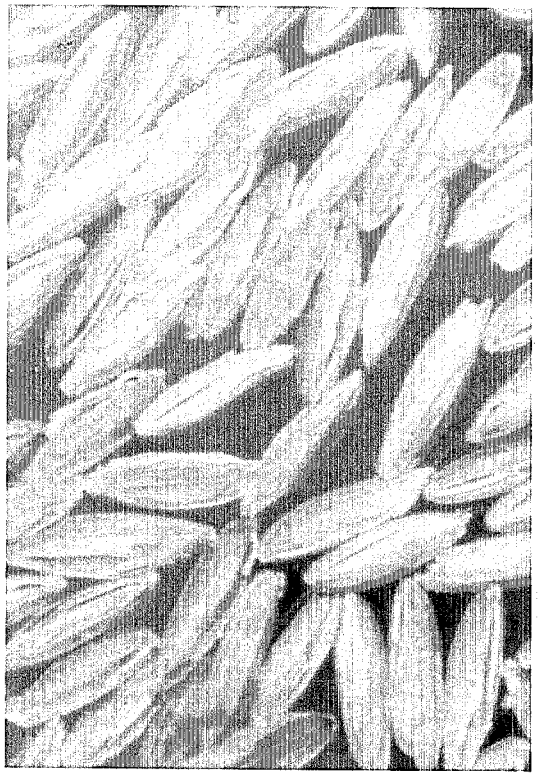
FIG. 2 is Ba 73-366 Kentucky bluegrass seed.
Figure 3:
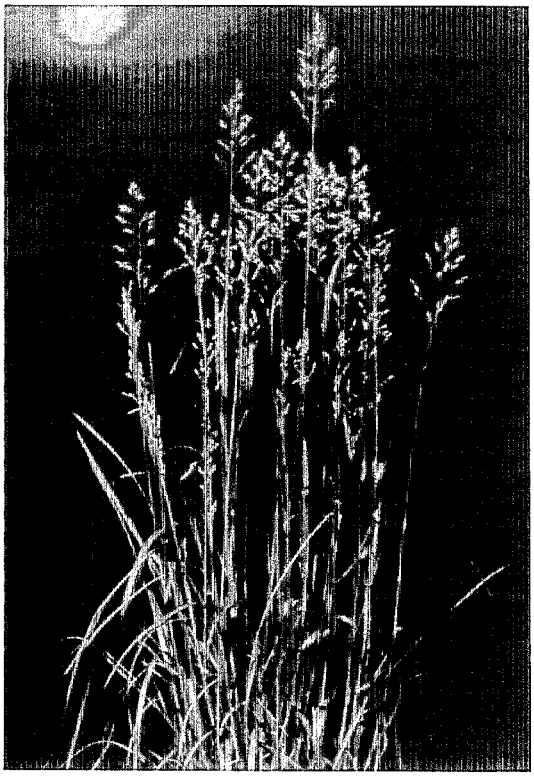
FIG. 3 is a Ba 73-366 Kentucky bluegrass plant shortly after completing anthesis.

Ba 73-366 Kentucky bluegrass (*Poa pratensis* L.) is perennial with creeping rhizomes forming a dense turf. When plants overwinter in the field under freezing temperatures and are then brought into the greenhouse during late winter to continue growth undisturbed by clipping under moderate temperatures (60°–80° F.), culms are erect averaging 42.7 cm in length with an average of 4.1 nodes per culm. The uppermost internode averages 9.2 cm and the peduncle averages 26.4 cm in length and 0.704 mm in width. The flag leaf averages 4.5 cm in length, 3.6 mm in width and 0.180 mm in thickness and a ligule length of 1.5 mm. The vegetative leaf averages 22.9 cm in length, 3.8 mm in width, 0.401 mm in thickness and a ligule length of 0.23 mm. The panicle has an average length of 88.88 mm, width of 68.4 mm, and 8.8 whorls. The lowest whorl has an average of 4.3 branches and the third whorl from the bottom of the panicle has an average of 3.7 branches. The average spikelet in the lowest whorl is 4.6 mm in length, 2.5 mm in width and has 2.6 florets with an outer glume of 2.8 mm and an inner glume of 3.2 mm in length. A spikelet from the third whorl from the bottom of the panicles is 4.7 mm in length, 2.6 mm in width and has 2.8 florets with an outer glume of 2.8 mm and an inner glume of 3.1 mm in length. Conditioned seed has an average amount of hair on the keel located on the dorsal side of the lemma. The seed of Ba 73-366 is 3.04 mm in length, 0.91 mm in width and a rachilla length of 0.80 mm with approximately 1,025,586 seeds per pound.

Comparisons of Ba 73-366 with other varieties in terms of seed dimensions and on seed numbers per pound are shown in Tables 1 and 2 as follows:

TABLE 1

Seed and Rachilla Measurements and Lemma Hair of Ba 73-366 and Other Kentucky Bluegrass Varieties After Conditioning.

| Variety | Length (mm) | Width (mm) | Rachilla (mm) | Lemma* Hair |
|---|---|---|---|---|
| Ba 73-366 | 3.04 | 0.91 | 0.80 | 4.4 |
| Abbey | 2.97 | 0.89 | 0.80 | 3.8 |
| Adelphi | 2.70 | 0.84 | 0.65 | 4.4 |
| America | 2.40 | 0.68 | 0.68 | 2.8 |
| Baron | 3.08 | 0.81 | 0.71 | 5.0 |
| Bristol | 2.94 | 0.88 | 0.73 | 4.3 |
| Chateau | 2.81 | 0.86 | 0.71 | 4.5 |
| Coventry | 2.71 | 0.81 | 0.70 | 4.0 |
| Eclipse | 2.77 | 0.83 | 0.68 | 3.5 |
| Georgetown | 2.94 | 0.82 | 0.74 | 4.9 |
| Gnome | 2.78 | 0.83 | 0.75 | 4.1 |
| Kelly | 3.07 | 0.89 | 0.75 | 4.2 |
| Marquis | 2.97 | 0.87 | 0.83 | 4.7 |
| Midnight | 2.94 | 0.76 | 0.78 | 5.7 |
| Nassau | 3.07 | 0.86 | 0.68 | 3.4 |
| Ram I | 3.23 | 0.89 | 0.80 | 6.0 |
| Touchdown | 2.93 | 0.88 | 0.71 | 4.6 |
| Victa | 3.00 | 0.80 | 0.82 | 3.5 |
| LSD (.05) | 0.16 | 0.05 | 0.13 | 0.86 |

*Rating Scale 0–9: 9 = abundant row of hairs along keel.

TABLE 2

Comparison of Seed Numbers Per Pound of Ba 73-366 and Other Bluegrass Varieties After Conditioning.

| Variety | Seeds per Pounds |
|---|---|
| Ba 73-366 | 1,025,586 |
| Abbey | 1,003,037 |
| Adelphi | 1,383,976 |
| America | 1,659,824 |
| Baron | 1,051,693 |
| Bristol | 1,270,821 |
| Chateau | 1,300,105 |
| Coventry | 1,246,200 |
| Eclipse | 1,335,668 |
| Georgetown | 1,431,000 |
| Gnome | 1,017,641 |
| Kelly | 921,166 |
| Marquis | 1,054,642 |
| Midnight | 1,227,000 |
| Nassua | 1,127,130 |
| Ram 1 | 1,214,000 |
| Touchdown | 1,211,000 |
| Victa | 1,038,298 |

Since environmental conditions such as soil and climate may influence morphological characteristics to some extent, comparisons of morphological characteristics of Ba 73-366 are made with other Kentucky bluegrass varieties in Tables 3–8.

TABLE 3

Morphological Comparison of Panicles of Ba 73-366 and Other Kentucky Bluegrass Varieties in the Greenhouse at Marysville, Ohio

| Variety | Panicle Nodding* | Panicle Length (mm) | Panicle Width (mm) | Number of Whorls Per Panicle | Number of Branches Lower Whorl | Number of Branches Third Whorl |
|---|---|---|---|---|---|---|
| Ba 73-366 | 1.6 | 88.8 | 68.4 | 8.8 | 4.3 | 3.7 |
| Abbey | 1.6 | 80.4 | 59.3 | 9.3 | 3.8 | 3.3 |
| Adelphi | 1.8 | 106.8 | 76.4 | 10.0 | 3.6 | 3.0 |
| America | 2.3 | 67.7 | 51.1 | 8.8 | 3.3 | 3.5 |
| Baron | 2.2 | 92.6 | 71.0 | 10.0 | 3.4 | 2.8 |
| Bristol | 2.0 | 85.5 | 61.5 | 8.4 | 2.8 | 2.7 |
| Chateau | 2.9 | 65.2 | 57.3 | 8.5 | 3.3 | 2.8 |
| Coventry | 2.5 | 64.0 | 54.2 | 8.4 | 3.3 | 2.5 |
| Eclipse | 1.3 | 89.2 | 74.0 | 10.7 | 3.3 | 2.1 |
| Georgetown | 1.0 | 80.0 | 57.0 | 7.4 | 2.1 | 2.6 |
| Gnome | 1.1 | 80.6 | 56.0 | 10.6 | 4.6 | 3.9 |
| Kelly | 2.0 | 88.0 | 70.2 | 9.8 | 4.6 | 3.7 |
| Marquis | 1.1 | 82.0 | 63.0 | 10.3 | 3.9 | 3.6 |
| Midnight | 2.0 | 75.8 | 48.4 | 7.1 | 2.9 | 3.0 |
| Nassau | 2.2 | 91.2 | 68.6 | 10.0 | 2.5 | 2.1 |
| Ram I | 1.3 | 67.7 | 47.0 | 7.3 | 3.0 | 3.2 |
| Touchdown | 1.1 | 73.1 | 75.0 | 7.6 | 2.1 | 2.3 |
| Victa | 1.7 | 74.9 | 58.3 | 10.0 | 4.7 | 3.5 |
| LSD (.05) | 0.68 | 7.35 | 8.62 | 0.66 | 0.72 | 0.5 |

*Panicle nodding rated 1–9: 1 = Erect; 9 = 90° nodding

TABLE 4

Morphological Comparison of Spikelets and Numbers of Florets of Ba 73-366 and Other Kentucky Bluegrass Varieties in the Greenhouse at Marysville, Ohio

| Variety | Spikelet Lower Whorl Length (mm) | Spikelet Lower Whorl Width (mm) | Spikelet Third Whorl Length (mm) | Spikelet Third Whorl Width (mm) | Number of Florets Per Spikelet Lower Whorl | Number of Florets Per Spikelet Third Whorl |
|---|---|---|---|---|---|---|
| Ba 73-366 | 4.6 | 2.5 | 4.72. | 2.6 | 2.6 | 2.8 |
| Abbey | 4.4 | 2.2 | 4.5 | 2.2 | 3.0 | 3.0 |
| Adelphi | 4.6 | 2.2 | 4.8 | 2.2 | 4.4 | 4.4 |
| America | 4.6 | 2.2 | 4.4 | 2.3 | 4.5 | 4.3 |
| Baron | 5.4 | 2.8 | 5.4 | 3.1 | 4.0 | 4.2 |
| Bristol | 4.9 | 2.4 | 5.0 | 2.5 | 4.2 | 4.5 |

TABLE 4-continued

Morphological Comparison of Spikelets and Numbers of Florets of Ba 73-366 and Other Kentucky Bluegrass Varieties in the Greenhouse at Marysville, Ohio

| | Spikelet | | | | Number of Florets Per Spikelet | |
|---|---|---|---|---|---|---|
| | Lower Whorl | | Third Whorl | | | |
| Variety | Length (mm) | Width (mm) | Length (mm) | Width (mm) | Lower Whorl | Third Whorl |
| Chateau | 4.4 | 2.4 | 4.4 | 2.4 | 3.4 | 3.5 |
| Coventry | 4.4 | 2.2 | 4.5 | 2.4 | 3.2 | 3.5 |
| Eclipse | 4.6 | 2.4 | 4.6 | 2.4 | 3.6 | 3.6 |
| Georgetown | 5.0 | 2.3 | 5.0 | 2.6 | 4.8 | 4.9 |
| Gnome | 4.6 | 2.5 | 4.6 | 2.9 | 3.2 | 3.2 |
| Kelly | 5.1 | 2.5 | 5.2 | 2.8 | 3.7 | 3.8 |
| Marquis | 4.3 | 2.2 | 4.4 | 2.3 | 3.1 | 2.9 |
| Midnight | 5.3 | 2.5 | 5.5 | 2.4 | 4.4 | 4.7 |
| Nassau | 4.7 | 2.6 | 4.8 | 3.0 | 4.2 | 4.3 |
| Ram I | 5.4 | 2.6 | 5.3 | 2.8 | 3.6 | 3.4 |
| Touchdown | 5.1 | 2.9 | 4.8 | 2.8 | 4.1 | 4.0 |
| Victa | 4.5 | 2.5 | 4.5 | 2.4 | 3.3 | 3.2 |
| LSD (.05) | 0.41 | 0.35 | 0.38 | 0.35 | 0.58 | 0.53 |

TABLE 5

Morphological Comparison of Glumes of Ba 73-366 and Other Kentucky Bluegrass Varieties in the Greenhouse at Marysville, Ohio

| | Glume Length | | | |
|---|---|---|---|---|
| | Outer | | Inner | |
| Variety | Lowest Whorl | Third Whorl | Lowest Whorl | Third Whorl |
| Ba 73-366 | 2.8 | 2.8 | 3.2 | 3.1 |
| Abbey | 2.7 | 2.7 | 3.1 | 3.1 |
| Adelphi | 2.7 | 2.6 | 3.0 | 3.1 |
| America | 2.1 | 2.1 | 2.5 | 2.5 |
| Baron | 3.1 | 3.2 | 3.6 | 3.7 |
| Bristol | 2.8 | 3.0 | 3.3 | 3.4 |
| Chateau | 2.8 | 2.9 | 3.1 | 3.2 |
| Coventry | 2.7 | 2.8 | 3.1 | 3.1 |
| Eclipse | 3.0 | 3.0 | 3.4 | 3.4 |
| Georgetown | 2.8 | 2.8 | 3.1 | 3.1 |
| Gnome | 2.8 | 2.9 | 3.3 | 3.3 |
| Kelly | 3.0 | 3.1 | 3.4 | 3.5 |
| Marquis | 2.8 | 2.7 | 3.1 | 3.1 |
| Midnight | 2.6 | 2.6 | 3.0 | 3.1 |
| Nassau | 2.6 | 2.7 | 2.9 | 3.0 |
| Ram I | 2.9 | 3.0 | 3.6 | 3.5 |
| Touchdown | 3.3 | 3.3 | 3.8 | 3.8 |
| Victa | 2.8 | 2.7 | 3.1 | 3.1 |
| LSD (.05) | 0.23 | 0.22 | 0.22 | 0.23 |

| | Glume Hairs | | | |
|---|---|---|---|---|
| Variety | Lowest Outer | Whorl Inner | Third Outer | Whorl Inner |
| Ba 73-366 | 1.7 | 1.3 | 1.3 | 2.0 |
| Abbey | 0.6 | 0.9 | 1.0 | 1.0 |
| Adelphi | 0.6 | 2.7 | 1.1 | 1.9 |
| America | 0.2 | 0.5 | 0.3 | 0.3 |
| Baron | 4.8 | 4.4 | 4.2 | 4.6 |
| Bristol | 1.0 | 2.2 | 0.8 | 2.2 |
| Chateau | 1.5 | 2.6 | 2.0 | 1.8 |
| Coventry | 1.5 | 2.7 | 1.6 | 2.4 |
| Eclipse | 1.5 | 1.9 | 1.8 | 1.9 |
| Georgetown | 1.7 | 2.7 | 1.2 | 2.5 |
| Gnome | 1.0 | 1.9 | 1.2 | 1.6 |
| Kelly | 1.3 | 1.5 | 1.1 | 0.8 |
| Marquis | 0.9 | 1.1 | 1.7 | 1.8 |
| Midnight | 1.8 | 2.8 | 1.0 | 2.4 |
| Nassau | 2.1 | 2.6 | 4.2 | 4.4 |
| Ram I | 1.1 | 2.3 | 0.7 | 1.2 |
| Touchdown | 0.7 | 2.1 | 1.1 | 1.4 |
| Victa | 0.8 | 1.1 | 1.1 | 1.3 |
| LSD (.05) | 0.85 | 0.92 | 0.89 | 0.87 |

TABLE 6

Morphological Comparison of Flag Leaves of Ba 73-366 and Other Kentucky Bluegrass Varieties in the Greenhouse at Marysville Ohio

| Variety | Length (cm) | Width (mm) | Thickness (mm) | Leaf Angle[a] |
|---|---|---|---|---|
| Ba 73-366 | 4.5 | 3.6 | 0.180 | 5.1 |
| Abbey | 3.8 | 3.4 | 0.145 | 2.7 |
| Adelphi | 5.7 | 3.4 | 0.178 | 5.2 |
| America | 4.3 | 2.6 | 0.211 | 4.6 |
| Baron | 7.0 | 4.2 | 0.152 | 9.2 |
| Bristol | 4.3 | 3.2 | 0.211 | 2.3 |
| Chateau | 4.0 | 2.7 | 0.193 | 3.4 |
| Coventry | 3.7 | 3.0 | 0.140 | 0.7 |
| Eclipse | 3.9 | 3.2 | 0.193 | 8.7 |
| Georgetown | 5.7 | 2.8 | 0.221 | 1.9 |
| Gnome | 4.5 | 3.5 | 0.185 | 4.3 |
| Kelly | 4.8 | 4.1 | 0.178 | 3.1 |
| Marquis | 5.5 | 3.6 | 0.241 | 2.7 |
| Midnight | 3.8 | 2.6 | 0.189 | 1.1 |
| Nassau | 6.0 | 3.7 | 0.191 | 5.9 |
| Ram I | 3.4 | 3.1 | 0.191 | 1.0 |
| Touchdown | 4.1 | 2.7 | 0.163 | 3.4 |
| Victa | 3.9 | 3.7 | 0.267 | 2.1 |
| LSD (.05) | 1.0 | 0.42 | 0.0249 | 2.49 |

| Variety | Leaf Curve[b] | Ligule (mm) | Leaf Margin | Ligule | Sheath Color |
|---|---|---|---|---|---|
| Ba 73-366 | 4.4 | 1.5 | 0.4 | 2.2 | 0.5 |
| Abbey | 4.1 | 1.3 | 0.8 | 1.6 | 0.2 |
| Adelphi | 5.0 | 1.1 | 1.8 | 1.6 | 0.4 |
| America | 5.0 | 0.6 | 0.4 | 0.7 | 1.9 |
| Baron | 4.4 | 1.2 | 1.0 | 3.8 | 2.6 |
| Bristol | 5.0 | 0.6 | 0.4 | 1.9 | 2.0 |
| Chateau | 2.0 | 0.9 | 1.1 | 3.1 | 0.3 |
| Coventry | 4.3 | 0.9 | 0.8 | 1.7 | 2.0 |
| Eclipse | 5.0 | 1.1 | 1.0 | 1.0 | 0.2 |
| Georgetown | 5.0 | 0.6 | 0.6 | 2.0 | 2.0 |
| Gnome | 5.0 | 0.8 | 0.9 | 3.2 | 1.5 |
| Kelly | 4.4 | 1.5 | 1.1 | 2.5 | 2.2 |
| Marquis | 4.6 | 0.8 | 0.5 | 3.8 | 1.5 |
| Midnight | 5.0 | 0.4 | 0.4 | 0.3 | 2.0 |
| Nassau | 4.7 | 1.1 | 2.6 | 2.4 | 0.8 |
| Ram I | 4.8 | 0.7 | 0.5 | 1.3 | 2.0 |
| Touchdown | 4.1 | 1.1 | 1.0 | 1.0 | 7.7 |
| Victa | 4.6 | 1.3 | 1.0 | 0.8 | 0.5 |
| LSD (.05) | 0.44 | 0.17 | 0.47 | 0.70 | 0.76 |

[a]Degrees from the stem
[b]Scale 1–9: 1 curve up; 5 no curve; 9 curves down

TABLE 7

Morphological Comparison of Peduncles, Culms, Node Numbers Per Culm and Internode Length of Ba 73-366 and Other Kentucky Bluegrass Varieties in the Greenhouse at Marysville, Ohio

| Variety | Peduncle Length (cm) | Peduncle Width (mm) | Culm Length (cm) | Number of Nodes Per Culm | Top Internode Length (cm) |
|---|---|---|---|---|---|
| Ba 73-366 | 26.4 | 0.704 | 42.7 | 4.1 | 9.2 |
| Abbey | 23.2 | 0.655 | 41.3 | 4.1 | 11.0 |
| Adelphi | 24.5 | 0.665 | 40.0 | 4.0 | 10.4 |
| America | 16.2 | 0.622 | 31.8 | 3.1 | 11.0 |
| Baron | 34.0 | 0.701 | 52.8 | 4.2 | 12.8 |
| Bristol | 22.9 | 0.734 | 43.5 | 4.0 | 12.6 |
| Chateau | 20.7 | 0.607 | 38.9 | 4.4 | 9.9 |
| Coventry | 19.6 | 0.487 | 34.7 | 4.5 | 7.9 |
| Eclipse | 23.7 | 0.658 | 39.2 | 4.9 | 9.9 |
| George-town | 21.7 | 0.683 | 37.5 | 3.2 | 11.1 |
| Gnome | 19.4 | 0.836 | 35.3 | 3.1 | 9.2 |
| Kelly | 29.4 | 0.752 | 46.6 | 3.6 | 11.8 |
| Marquis | 27.1 | 0.831 | 34.1 | 3.4 | 7.8 |
| Midnight | 20.5 | 0.722 | 29.5 | 2.8 | 7.6 |
| Nassau | 25.0 | 0.663 | 36.0 | 3.9 | 7.4 |
| Ram I | 22.2 | 0.694 | 30.5 | 2.5 | 6.6 |
| Touch-down | 23.6 | 0.519 | 38.0 | 4.0 | 8.4 |
| Victa | 21.2 | 0.808 | 37.9 | 3.7 | 10.3 |
| LSD (.05) | 3.17 | 0.774 | 3.32 | 0.44 | 1.94 |

TABLE 8

Morphological Comparison of Vegetative Leaves of Ba 73-366 and Other Kentucky Bluegrass Varieties in the Greenhouse at Marysville Ohio

| Variety | Length (cm) | Width (mm) | Thickness (mm) | Leaf Angle[a] | Leaf Curvature[b] |
|---|---|---|---|---|---|
| Ba 73-366 | 22.9 | 3.8 | 0.401 | 53.0 | 7.1 |
| Abbey | 20.7 | 3.6 | 0.277 | 51.3 | 7.4 |
| Adelphi | 19.4 | 3.7 | 0.279 | 67.0 | 4.6 |
| America | 21.4 | 3.1 | 0.325 | 66.0 | 6.4 |
| Baron | 18.2 | 4.3 | 0.290 | 35.0 | 4.4 |
| Bristol | 18.2 | 3.7 | 0.320 | 65.5 | 6.9 |
| Chateau | 23.1 | 3.3 | 0.328 | 39.7 | 5.4 |
| Coventry | 23.4 | 3.6 | 0.249 | 63.0 | 7.3 |
| Eclipse | 20.3 | 4.4 | 0.302 | 65.5 | 5.4 |
| Georgetown | 19.5 | 3.6 | 0.287 | 56.7 | 5.8 |
| Gnome | 18.2 | 2.9 | 0.290 | 43.2 | 6.6 |
| Kelly | 22.8 | 3.9 | 0.300 | 55.5 | 7.0 |
| Marquis | 19.7 | 3.7 | 0.376 | 46.4 | 7.8 |
| Midnight | 19.5 | 3.5 | 0.310 | 63.3 | 5.0 |
| Nassau | 16.3 | 3.7 | 0.292 | 63.2 | 4.9 |
| Ram I | 19.1 | 3.6 | 0.271 | 70.8 | 6.5 |
| Touchdown | 16.7 | 3.7 | 0.243 | 51.3 | 4.0 |
| Victa | 21.5 | 3.6 | 0.361 | 56.3 | 6.7 |
| LSD (.05) | 3.49 | 0.43 | 0.0439 | 15.90 | 1.54 |

| Variety | Ligule Length (mm) | Hairs[c] Ligule | Hairs[c] Collar | Hairs[c] Leaf Margin | Leaf[d] Roughness | Sheath Color[e] |
|---|---|---|---|---|---|---|
| Ba 73-366 | 0.23 | 5.2 | 0.0 | 4.2 | 8.5 | 0.0 |
| Abbey | 0.32 | 4.4 | 0.0 | 2.8 | 7.7 | 0.0 |
| Adelphi | 0.34 | 2.6 | 0.0 | 3.4 | 8.8 | 0.0 |
| America | 0.12 | 1.7 | 0.0 | 2.1 | 8.4 | 2.0 |
| Baron | 0.33 | 4.6 | 0.0 | 3.6 | 7.4 | 0.4 |
| Bristol | 0.12 | 2.6 | 0.0 | 3.0 | 8.9 | 2.0 |
| Chateau | 0.22 | 3.3 | 0.0 | 3.1 | 7.8 | 0.5 |
| Coventry | 0.32 | 3.1 | 0.0 | 2.4 | 8.1 | 0.3 |
| Eclipse | 0.38 | 2.8 | 0.0 | 2.6 | 9.0 | 0.2 |
| Georgetown | 0.14 | 2.5 | 0.0 | 2.4 | 8.5 | 2.0 |
| Gnome | 0.23 | 1.6 | 0.9 | 0.8 | 7.5 | 1.4 |
| Kelly | 0.34 | 4.6 | 0.0 | 2.4 | 8.8 | 0.0 |
| Marquis | 0.21 | 3.6 | 0.3 | 1.1 | 6.8 | 1.1 |
| Midnight | 0.10 | 1.3 | 0.0 | 1.6 | 7.7 | 2.0 |
| Nassau | 0.34 | 2.5 | 0.0 | 3.3 | 8.5 | 1.4 |
| Ram I | 0.09 | 1.8 | 0.0 | 2.0 | 7.7 | 2.0 |
| Touchdown | 0.29 | 1.4 | 0.0 | 1.3 | 7.9 | 8.0 |
| Victa | 0.26 | 2.3 | 0.0 | 1.7 | 7.9 | 0.1 |
| LSD (.05) | 0.04 | 0.79 | 0.21 | 0.70 | 0.89 | 0.57 |

[a]Degrees from stem
[b]Scale 1–9: 1 = curvature up; 5 = no curvature; 9 = curvature down
[c]Scale 0–9: 0 = none 9 = many
[d]Scale 1–9: 1 = rough 9 = smooth
[e]Scale 0–9: 0 = no color 9 = dark purple Ba 73-366 has performed well in regions throughout the U.S.A., as exhibited by a good to high level of turf quality ratings in a number of locations in comparison to other varieties. In addition, Ba 73-336 has a pleasant medium green color which can be maintained throughout the growing season, and has good winter color. Comparisons of Ba 73-366 with other varieties for quality, genetic color and winter color are set forth hereinafter in Tables 9–11. During mid-May while the turf was actively growing with adequate nutrient and water availability, readings of the vegetative color of Ba 73-366 were taken in full sun with several actively growing leaves being compared, one at a time, utilizing color chips from the Munsell Book of Color as a reference. On this basis, the color of Ba 73-366 was determined to be 5 GY 4/4. During the same time period, the color of similar leaves of other Kentucky Bluegrass varieties were determined by the same procedure to be as follows: Ba 73-540 - 5 GY 4/4; Abbey - 5 GY 3/4; and Coventry - 5 GY 4/4.

TABLE 9

Comparison of Turfgrass Quality of Ba 73-366 and Other Kentucky Bluegrass Varieties at Various Locations in the U.S.A.

| Variety | Locations[a] A | B | C | D | E | F | G | H | I | Mean |
|---|---|---|---|---|---|---|---|---|---|---|
| Ba 73-366 | 7.7 | 7.2 | 5.5 | 5.3 | 6.5 | 5.0 | 5.2 | 6.6 | 6.2 | 5.5 |
| Abbey | 7.0 | 6.9 | 6.2 | 5.5 | 5.4 | 5.1 | 3.5 | 6.8 | 6.6 | 5.5 |
| Able I | 7.7 | 7.5 | 5.4 | 5.9 | 7.0 | 5.7 | 5.9 | 6.5 | 5.8 | 5.8 |
| A-34 | 8.7 | 6.8 | 5.2 | 4.6 | 7.0 | 5.4 | 5.3 | 6.2 | 4.8 | 5.6 |
| Banff | 8.7 | 6.6 | 6.6 | 6.1 | 6.8 | 4.6 | 5.1 | 6.7 | 6.6 | 6.0 |
| Baron | 7.7 | 7.2 | 6.4 | 5.7 | 7.0 | 5.7 | 5.3 | 7.0 | 6.0 | 5.8 |
| Challenger | 8.7 | 6.6 | 5.2 | 4.9 | 6.7 | 5.7 | 5.7 | 6.6 | 5.6 | 5.8 |
| Classic | 8.3 | 6.9 | 5.6 | 6.2 | 6.8 | 4.3 | 5.6 | 6.7 | 5.8 | 5.8 |
| Coventry | 8.7 | 6.3 | 6.5 | 5.9 | 6.7 | 5.8 | 5.3 | 7.0 | 6.4 | 5.9 |
| Eclipse | 8.3 | 6.7 | 6.9 | 6.5 | 6.2 | 5.1 | 5.9 | 7.3 | 5.7 | 5.9 |
| Estate | 8.7 | 7.0 | 6.0 | 5.5 | 7.0 | 6.0 | 5.7 | 6.4 | 5.9 | 5.9 |
| Georgetown | 8.0 | 6.6 | 6.0 | 6.6 | 6.5 | 4.9 | 5.7 | 6.9 | 6.6 | 5.9 |
| Glade | 9.0 | 7.4 | 6.8 | 7.5 | 7.0 | 5.6 | 4.5 | 7.6 | 6.9 | 6.2 |
| Gnome | 8.0 | 6.8 | 5.8 | 5.0 | 7.0 | 5.0 | 4.8 | 7.0 | 4.9 | 5.5 |
| Haga | 8.0 | 6.7 | 6.4 | 6.3 | 7.0 | 5.1 | 5.7 | 6.8 | 6.3 | 5.9 |
| Kelly | 7.7 | 7.2 | 6.0 | 5.8 | 6.5 | 5.0 | 5.2 | 6.8 | 5.6 | 5.5 |
| Kenblue | 7.7 | 6.4 | 4.9 | 3.3 | 7.0 | 3.8 | 3.2 | 6.2 | 5.3 | 4.6 |
| Marquis | 8.0 | 6.8 | 5.4 | 5.3 | 6.7 | 5.5 | 4.7 | 6.5 | 5.0 | 5.4 |
| Merion | 6.7 | 5.1 | 3.8 | 2.7 | 5.2 | 4.2 | 4.8 | 4.8 | 4.4 | 4.2 |
| Midnight | 8.0 | 7.1 | 6.7 | 8.3 | 6.7 | 4.7 | 5.7 | 7.7 | 5.4 | 6.2 |
| Monopoly | 7.7 | 6.5 | 6.0 | 5.0 | 7.3 | 4.8 | 5.1 | 6.1 | 5.2 | 5.3 |
| Nassau | 8.0 | 6.9 | 6.0 | 6.4 | 6.0 | 5.5 | 5.5 | 6.3 | 5.9 | 5.6 |
| Ram I | 8.0 | 7.8 | 5.3 | 6.0 | 7.3 | 5.2 | 5.2 | 7.0 | 7.0 | 6.1 |
| South Dakota | 7.0 | 6.6 | 4.7 | 3.0 | 6.2 | 2.1 | 2.7 | 4.9 | 4.4 | 4.1 |
| Touchdown | 9.0 | 7.2 | 5.3 | 4.2 | 6.7 | 3.3 | 5.1 | 6.5 | 6.3 | 5.5 |
| LSD (.05) | 1.2 | 0.8 | 1.0 | 0.9 | 1.1 | 1.1 | 0.5 | 0.5 | 1.2 | 0.3 |

Quality Rating Scale 1–9; 9 = ideal turf
[a]Locations: A. Fort Collins, CO; B. Ames, Iowa; C. Post Falls, ID; D. Levington, KY; E. Marysville, OH; F. Hubbard, OR; G. Pooled data from Halsey, Hubbard and Gervais, OR; H. Beltsville, MD; I. Pullman, WA

TABLE 10

A Comparison of Genetic Color of Ba 73-366 and Other Kentucky Bluegrasses at Various Locations in the U.S.A.

| Variety | Locations[a] A | B | C | D | E | F | G | Mean |
|---|---|---|---|---|---|---|---|---|
| Ba 73-366 | 4.7 | 5.7 | 4.3 | 4.3 | 7.0 | 7.0 | 5.7 | 5.5 |
| Abbey | 4.0 | 6.2 | 5.3 | 4.3 | 7.0 | 6.0 | 6.7 | 5.6 |
| Able I | 4.7 | 7.3 | 8.0 | 6.0 | 7.3 | 7.0 | 6.0 | 6.6 |
| A-34 | 4.0 | 5.0 | 3.7 | 4.3 | 6.7 | 6.0 | 5.3 | 5.0 |
| Banff | 5.7 | 4.7 | 4.0 | 5.0 | 6.7 | 6.0 | 4.0 | 5.1 |
| Baron | 4.0 | 6.0 | 6.0 | 5.0 | 7.3 | 7.3 | 6.3 | 6.0 |
| Challenger | 4.7 | 6.2 | 6.0 | 5.0 | 7.3 | 7.0 | 5.7 | 6.0 |
| Classic | 5.3 | 5.2 | 4.3 | 5.0 | 6.7 | 5.7 | 4.3 | 5.2 |
| Coventry | 5.3 | 5.8 | 5.7 | 4.3 | 7.0 | 6.7 | 6.3 | 5.9 |
| Eclipse | 5.0 | 7.0 | 6.3 | 5.3 | 7.3 | 6.3 | 7.0 | 6.3 |
| Estate | 4.7 | 6.2 | 5.7 | 5.3 | 6.7 | 6.7 | 5.7 | 5.8 |
| Georgetown | 4.0 | 5.0 | 4.7 | 5.0 | 7.0 | 6.0 | 5.0 | 5.2 |
| Glade | 5.3 | 7.3 | 7.0 | 6.0 | 7.0 | 7.0 | 7.3 | 6.7 |
| Gnome | 5.3 | 5.5 | 5.7 | 4.7 | 7.3 | 7.0 | 6.7 | 6.0 |
| Haga | 4.3 | 5.0 | 4.0 | 5.0 | 7.0 | 6.0 | 4.3 | 5.1 |
| Kelly | 4.7 | 6.2 | 4.7 | 4.0 | 7.0 | 6.3 | 6.3 | 5.6 |
| Kenblue | 3.7 | 4.3 | 3.7 | 3.7 | 7.0 | 6.0 | 4.0 | 4.6 |
| Marquis | 5.0 | 6.5 | 5.3 | 5.0 | 7.3 | 7.0 | 6.7 | 6.1 |
| Merion | 4.3 | 6.7 | 6.3 | 4.3 | 7.0 | 5.3 | 6.0 | 5.7 |
| Midnight | 6.0 | 7.7 | 8.3 | 6.3 | 8.0 | 7.7 | 6.0 | 7.1 |
| Monopoly | 4.7 | 4.2 | 4.0 | 4.0 | 6.0 | 6.7 | 4.0 | 4.8 |
| Nassau | 5.7 | 6.7 | 5.7 | 5.0 | 8.0 | 6.7 | 4.7 | 6.0 |
| Ram I | 6.0 | 7.0 | 7.0 | 6.0 | 7.3 | 7.0 | 6.7 | 6.7 |
| South Dakota | 4.0 | 5.2 | 3.0 | 3.0 | 7.0 | 5.3 | 4.0 | 4.5 |
| Touchdown | 4.7 | 6.3 | 4.3 | 4.7 | 7.3 | 6.3 | 5.0 | 5.5 |
| LSD (.05) | 1.3 | 1.3 | 0.9 | 0.7 | 0.7 | 0.7 | 1.4 | 0.5 |

Genetic Color Quality Rating Scale 1–9; 9 = ideal turf
[a]Locations: A. Fort Collins, CO; B. Post Falls, ID; C. North Brunswick, NJ; D. Martinsville, NJ; E. Marysville, OH; F. Pooled data from Halsey, Hubbard and Gervais, OR G. Haymarket, VA;

TABLE 11

Comparison of Winter Color of Ba 73-366 and Other Kentucky Bluegrasses Based on Data From Various at Locations in the U.S.A.

| Variety | Locations A | B | Mean |
|---|---|---|---|
| Ba 73-366 | 3.0 | 5.7 | 4.3 |
| Abbey | 3.3 | 5.7 | 4.5 |
| Able I | 4.0 | 7.0 | 5.5 |
| A-34 | 4.0 | 4.3 | 4.2 |
| Banff | 4.0 | 5.0 | 4.5 |
| Baron | 3.7 | 3.7 | 3.7 |
| Challenger | 3.7 | 6.3 | 5.0 |
| Classic | 4.0 | 5.7 | 4.8 |
| Coventry | 2.7 | 4.3 | 3.5 |
| Eclipse | 3.3 | 5.7 | 4.5 |
| Estate | 3.7 | 5.3 | 4.5 |
| Georgetown | 4.7 | 7.0 | 5.8 |
| Glade | 2.7 | 4.7 | 3.7 |
| Gnome | 2.7 | 4.3 | 3.5 |
| Haga | 3.3 | 5.3 | 4.3 |
| Kelly | 3.0 | 5.3 | 4.2 |
| Kenblue | 3.3 | 2.7 | 3.0 |
| Marquis | 3.3 | 4.0 | 3.7 |
| Merion | 2.3 | 6.3 | 4.3 |
| Midnight | 3.3 | 5.3 | 4.3 |
| Monopoly | 3.3 | 5.0 | 4.2 |
| Nassau | 3.0 | 5.7 | 4.3 |
| Ram I | 3.7 | 6.0 | 4.8 |
| South Dakota | 1.7 | 2.0 | 1.8 |
| Touchdown | 3.3 | 5.3 | 4.3 |
| LSD (.05) | 1.0 | 1.6 | 0.9 |

Color Rating Scale 1–9; 9 = complete color retention

Locations: A. Martinsville, NJ B. Pooled data from Halsey, Hubbard and Gervais, OR Ba 73-366 develops good density and a high degree of living ground cover in the spring and summer. It has a moderately wide blade as identified by leaf texture data. Also Ba 73-366 has good seedling vigor. Data for these performance characteristics are presented in Table 12–15.

TABLE 12

Comparison of Summer Density of Ba 73-366 and other Kentucky Bluegrasses at Various Locations in the U.S.A.

| | Locations Post Falls Idaho | Martinsville NJ | Marysville OH | Kingston RI | Mean |
|---|---|---|---|---|---|
| Ba 73-366 | 6.7 | 4.3 | 6.3 | 4.0 | 5.3 |
| Abbey | 6.0 | 5.7 | 6.0 | 3.0 | 5.2 |
| Able I | 7.7 | 5.0 | 7.0 | 4.3 | 6.0 |
| A-34 | 7.0 | 4.7 | 6.0 | 5.0 | 5.7 |
| Banff | 6.7 | 4.7 | 6.3 | 4.0 | 5.4 |
| Baron | 6.7 | 5.3 | 6.3 | 4.3 | 5.7 |
| Challenger | 7.7 | 5.7 | 6.7 | 4.0 | 6.0 |
| Classic | 7.0 | 5.7 | 6.7 | 4.7 | 6.0 |
| Coventry | 7.0 | 6.0 | 6.7 | 4.0 | 5.9 |
| Eclipse | 5.7 | 6.3 | 6.3 | 4.0 | 5.6 |
| Estate | 7.0 | 5.3 | 7.3 | 4.7 | 6.1 |
| Georgetown | 6.7 | 5.7 | 6.3 | 4.3 | 5.8 |
| Glade | 8.3 | 4.7 | 6.7 | 4.0 | 5.9 |
| Gnome | 7.0 | 5.3 | 6.3 | 4.3 | 5.8 |
| Haga | 6.7 | 5.7 | 6.3 | 4.3 | 5.8 |
| Kelly | 6.7 | 4.3 | 6.0 | 3.3 | 5.1 |
| Kenblue | 7.3 | 3.7 | 6.0 | 3.7 | 5.2 |
| Marquis | 6.7 | 5.3 | 6.3 | 4.0 | 5.7 |
| Merion | 3.3 | 4.3 | 4.7 | 1.7 | 3.5 |
| Midnight | 7.7 | 6.3 | 6.3 | 3.7 | 6.0 |

TABLE 12 -continued

Comparison of Summer Density of Ba 73-366 and other Kentucky Bluegrasses at Various Locations in the U.S.A.

| | Locations Post Falls Idaho | Martinsville NJ | Marysville OH | Kingston RI | Mean |
|---|---|---|---|---|---|
| Monopoly | 5.7 | 4.7 | 6.7 | 4.0 | 5.3 |
| Nassau | 6.0 | 5.0 | 5.7 | 3.7 | 5.1 |
| Ram I | 8.3 | 5.3 | 7.0 | 4.0 | 6.2 |
| South Dakota | 7.0 | 2.0 | 5.7 | 3.7 | 4.6 |
| Touchdown | 8.0 | 5.3 | 6.0 | 3.0 | 5.6 |
| LSD (.05) | 1.6 | 1.4 | 1.2 | 1.2 | 0.7 |

Density Rating Scale 1–9; 9 = maximum density

TABLE 13

Comparison of Percent Living Ground Cover in the Spring of Ba 73-366 and other Kentucky Bluegrasses at Various Locations in the U.S.A. and Canada

| | Locations Post Falls Idaho | Carbondale Illinois | Richmond Ont. | Mean |
|---|---|---|---|---|
| Ba 73-366 | 78.3 | 65.0 | 33.3 | 58.9 |
| Abbey | 53.3 | 51.7 | 30.0 | 45.0 |
| Able I | 81.7 | 43.3 | 30.0 | 51.7 |
| A-34 | 61.7 | 68.3 | 33.3 | 54.4 |
| Banff | 80.0 | 76.3 | 43.3 | 66.6 |
| Baron | 45.0 | 51.0 | 40.0 | 45.3 |
| Challenger | 63.3 | 56.7 | 26.7 | 48.9 |
| Classic | 60.0 | 75.0 | 43.3 | 59.4 |
| Coventry | 85.0 | 43.3 | 30.0 | 52.8 |
| Eclipse | 26.7 | 31.7 | 26.7 | 28.3 |
| Estate | 61.7 | 79.7 | 33.3 | 58.2 |
| Georgetown | 76.7 | 76.0 | 30.0 | 60.9 |
| Glade | 73.3 | 51.7 | 40.0 | 55.0 |
| Gnome | 66.7 | 40.0 | 26.7 | 44.4 |
| Haga | 63.3 | 65.0 | 33.3 | 53.9 |
| Kelly | 65.0 | 50.7 | 40.0 | 51.9 |
| Kenblue | 73.3 | 91.0 | 36.7 | 67.0 |
| Marquis | 63.3 | 44.0 | 30.0 | 45.8 |
| Merion | 5.7 | 14.0 | 20.0 | 13.2 |
| Midnight | 38.3 | 20.7 | 26.7 | 28.6 |
| Monopoly | 65.0 | 90.3 | 33.3 | 62.9 |
| Nassau | 60.0 | 45.0 | 30.0 | 45.0 |
| Ram I | 71.7 | 76.7 | 36.7 | 61.7 |
| South Dakota | 71.7 | 88.7 | 36.7 | 65.7 |
| Touchdown | 56.7 | 38.3 | 36.7 | 43.9 |
| LSD (.05) | 30.0 | 41.0 | 14.4 | 17.6 |

TABLE 14

Comparison of Leaf Texture of Ba 73-366 and Other Kentucky Bluegrasses at Martinsville, New Jersey

| Variety | Leaf Texture |
|---|---|
| Ba 73-366 | 4.3 |
| Abbey | 5.0 |
| Able I | 5.7 |
| A-34 | 4.3 |
| Banff | 5.3 |
| Baron | 5.0 |
| Challenger | 5.0 |
| Classic | 5.3 |
| Coventry | 5.0 |
| Eclipse | 5.7 |
| Estate | 4.3 |
| Georgetown | 6.0 |
| Glade | 5.0 |
| Gnome | 5.3 |
| Haga | 5.7 |
| Kelly | 4.3 |
| Kenblue | 6.0 |
| Marquis | 4.3 |
| Merion | 4.0 |
| Midnight | 6.7 |

TABLE 14-continued

Comparison of Leaf Texture of Ba 73-366 and Other Kentucky Bluegrasses at Martinsville, New Jersey

| Variety | Leaf Texture |
|---|---|
| Monopoly | 5.0 |
| Nassau | 5.0 |
| Ram I | 5.0 |
| South Dakota | 3.7 |
| Touchdown | 5.3 |
| LSD (.05) | 0.9 |

Leaf Texture Rating Scale 1–9; 9 = very fine

TABLE 15

Comparison of Seedling Vigor of Ba 73-366 and Other Kentucky Bluegrass Varieties at Various Locations in the U.S.A. and Canada[a]

| Variety | Seedling Vigor Mean |
|---|---|
| Ba 73-366 | 6.3 |
| Abbey | 6.4 |
| Able I | 6.3 |
| A-34 | 6.0 |
| Banff | 7.7 |
| Baron | 6.7 |
| Challenger | 5.6 |
| Classic | 7.1 |
| Coventry | 6.1 |
| Eclipse | 6.1 |
| Estate | 6.1 |
| Georgetown | 7.0 |
| Glade | 6.7 |
| Gnome | 6.3 |
| Haga | 7.1 |
| Kelly | 6.6 |
| Kenblue | 7.4 |
| Marquis | 6.3 |
| Merion | 2.6 |
| Midnight | 5.4 |
| Monopoly | 7.1 |
| Nassau | 6.4 |
| Ram I | 6.5 |
| South Dakota | 6.7 |
| Touchdown | 5.8 |
| LSD (.05) | 0.7 |

Vigor Rating Scale 1–9; 9 = maximum vigor
[a]Locations: Fort Collins, CO; Post Falls, ID; North Brunswick, NJ; Adelphia, NJ; Richmond Hill, Ontario; Pooled data from Halsey, Hubbard and Gervais, OR.

Turf diseases are one of the major causes of inconsistent and poor turf performance. Ba 73-366 has been found to have a medium to high level of resistance to a serious bluegrass disease known as leaf spot (also known as melting out) caused by *Drechslera poae* (formerly called *Helminthosporium vagans*); a medium to high level of resistance to several rust diseases caused by Puccinia spp.; and medium to high level of resistance to dollarspot caused by *Sclerotinia homoeocarpa*. Comparisons of disease incidence of Ba 73-366 as compared with other bluegrass varieties in regard to leaf spot, rusts, powdery mildew and dollarspot are set forth in Tables 16–21. Additional comparisons are presented in Tables 22–25 identifying good drought tolerance and high seed yields relative to other bluegrasses.

TABLE 16

Comparison of Leaf Spot Incidence of Ba 73-366 and Other Kentucky Bluegrass Varieties Grown Under Shade Conditions at Marysville, Ohio

| Variety | % Leaf Spot |
|---|---|
| Ba 73-366 | 0.0 |
| Adelphi | 5.0 |
| America | 40.0 |
| Banff | 2.5 |

TABLE 16-continued

Comparison of Leaf Spot Incidence of Ba 73-366 and Other Kentucky Bluegrass Varieties Grown Under Shade Conditions at Marysville, Ohio

| Variety | % Leaf Spot |
|---|---|
| Bristol | 0.0 |
| Classic | 5.0 |
| Eclipse | 2.5 |
| Georgetown | 7.5 |
| Glade | 7.5 |
| Kenblue | 10.0 |
| Merion | 0.0 |
| Nassau | 0.0 |
| Newport | 0.0 |
| Park | 50.0 |
| Ram I | 40.0 |
| Sydsport | 27.5 |
| Vantage | 2.5 |
| Victa | 2.5 |
| Mean | 9.8 |
| LSD (.05) | 26.7 |

Leaf Spot Rating = % area covered by disease

TABLE 17

Comparison of Dollar Spot Incidence of Ba 73-366 and Other Kentucky Bluegrass Varieties at Kingston, R.I.

| Variety | Dollar Spot |
|---|---|
| Ba 73-366 | 8.3 |
| Abbey | 8.0 |
| Able I | 8.3 |
| A-34 | 7.7 |
| Banff | 7.7 |
| Baron | 7.7 |
| Challenger | 8.0 |
| Classic | 8.0 |
| Coventry | 7.7 |
| Eclipse | 8.3 |
| Estate | 8.3 |
| Georgetown | 8.0 |
| Glade | 7.7 |
| Gnome | 8.0 |
| Haga | 7.7 |
| Kelly | 8.0 |
| Kenblue | 8.0 |
| Marquis | 8.0 |
| Merion | 7.7 |
| Midnight | 8.3 |
| Monopoly | 8.0 |
| Nassau | 8.0 |
| Ram I | 7.3 |
| South Dakota | 8.0 |
| Touchdown | 8.0 |
| LSD (.05) | 0.9 |

Dollar Spot Rating 1–9; 9 = no disease

TABLE 18

Comparison of Powdery Mildew Incidence of Ba 73-366 and Other Kentucky Bluegrass Varieties Grown Under Shade Conditions at Marysville, Ohio

| | % Powdery Mildew | |
|---|---|---|
| Variety | Test 1 | Test 2 |
| Ba 73-366 | 80.0 | 27.5 |
| Adelphi | 35.0 | 37.5 |
| Bristol | 30.0 | 17.5 |
| Dormie | 30.0 | 27.5 |
| Glade | 35.0 | 45.0 |
| Merion | 75.0 | 67.5 |
| Monopoly | 7.5 | 15.0 |
| Nassau | 27.5 | 45.0 |
| Park | 50.0 | 35.0 |
| Ram I | 50.0 | 42.5 |
| Vantage | 37.5 | 10.0 |
| Victa | 87.5 | 50.0 |
| Wabash | 25.0 | 5.0 |
| Mean | 48.0 | 35.6 |
| LSD (.05) | 43.0 | 22.0 |

TABLE 19

Comparison of Stem Rust Incidence of Ba 73-366 and Other Kentucky Bluegrass varieties at Kingston, R.I.

| Variety | Stem Rust |
|---|---|
| Ba 73-366 | 6.7 |
| Abbey | 7.0 |
| Able I | 3.3 |
| A-34 | 4.3 |
| Banff | 7.7 |
| Baron | 7.0 |
| Challenger | 4.0 |
| Classic | 8.0 |
| Coventry | 6.7 |
| Eclipse | 4.0 |
| Estate | 6.3 |
| Georgetown | 8.7 |
| Glade | 7.7 |
| Gnome | 7.0 |
| Haga | 8.0 |
| Kelly | 8.0 |
| Kenblue | 5.7 |
| Marquis | 6.7 |
| Merion | 1.0 |
| Midnight | 8.0 |
| Monopoly | 6.3 |
| Nassau | 8.0 |
| Ram I | 8.0 |
| South Dakota | 4.3 |
| Touchdown | 2.3 |
| LSD (.05) | 1.4 |

Stem Rust Rating 1-9; 9 = no disease

TABLE 20

Comparison of Leaf Rust Incidence of Ba 73-366 and Other Kentucky Bluegrass Varities at Kingston, R.I.

| Variety | Leaf Rust |
|---|---|
| Ba 73-366 | 5.7 |
| Abbey | 6.3 |
| Able I | 7.0 |
| A-34 | 6.0 |
| Banff | 7.0 |
| Baron | 8.3 |
| Challenger | 5.7 |
| Classic | 8.7 |
| Coventry | 7.0 |
| Eclipse | 5.7 |
| Estate | 6.3 |
| Georgetown | 7.7 |
| Glade | 7.0 |
| Gnome | 6.7 |
| Haga | 7.0 |
| Kelly | 5.0 |
| Kenblue | 6.7 |
| Marquis | 6.3 |
| Merion | 2.3 |
| Midnight | 6.0 |
| Monopoly | 5.3 |
| Nassau | 7.0 |
| Ram I | 6.7 |
| South Dakota | 6.7 |
| Touchdown | 3.7 |
| LSD (.05) | 2.4 |

Leaf Rust Rating 1-9; 9 = no disease

TABLE 21

Comparison of Stripe Rust Incidence of Ba 73-366 and Other K28 Kentucky Bluegrass Varieties at Various Locations in Oregon

| Variety | Stripe Rust[a] |
|---|---|
| Ba 73-366 | 5.0 |
| Abbey | 4.3 |
| Able I | 6.0 |
| A-34 | 5.0 |
| Banff | 6.0 |
| Baron | 6.0 |
| Challenger | 5.3 |
| Classic | 6.3 |

TABLE 21-continued

Comparison of Stripe Rust Incidence of Ba 73-366 and Other K28 Kentucky Bluegrass Varieties at Various Locations in Oregon

| Variety | Stripe Rust[a] |
|---|---|
| Coventry | 5.0 |
| Eclipse | 6.0 |
| Estate | 5.7 |
| Georgetown | 6.3 |
| Glade | 3.0 |
| Gnome | 4.7 |
| Haga | 6.3 |
| Kelly | 5.0 |
| Kenblue | 3.3 |
| Marquis | 5.3 |
| Merion | 3.7 |
| Midnight | 4.7 |
| Monopoly | 5.3 |
| Nassau | 5.3 |
| Ram I | 6.0 |
| South Dakota | 4.0 |
| Touchdown | 3.0 |
| LSD (.05) | 1.2 |

Stripe Rust Rating 1-9; 9 = no disease

[a]Locations: Pooled data from Halsey, Hubbard and Gervais, Oregon.

TABLE 22

Comparison of Drought Tolerance as Recovery of Ba 73-366 and Other Kentucky Bluegrass Varieties at Various Locations in the U.S.A. 1991

| Variety | Carbondale Illinois | Oregon[a] | Mean |
|---|---|---|---|
| Ba 73-366 | 5.0 | 4.7 | 4.8 |
| Abbey | 5.0 | 4.0 | 4.5 |
| Able I | 4.7 | 4.0 | 4.3 |
| A-34 | 5.3 | 1.3 | 3.3 |
| Banff | 4.7 | 2.3 | 3.5 |
| Baron | 4.7 | 6.3 | 5.5 |
| Challenger | 5.0 | 2.0 | 3.5 |
| Classic | 4.7 | 3.7 | 4.2 |
| Coventry | 5.7 | 3.7 | 4.7 |
| Eclipse | 5.0 | 1.7 | 3.3 |
| Estate | 4.7 | 6.3 | 5.5 |
| Georgetown | 4.3 | 2.7 | 3.5 |
| Glade | 4.7 | 3.9 | 4.2 |
| Gnome | 4.7 | 5.0 | 4.8 |
| Haga | 5.3 | 2.7 | 4.0 |
| Kelly | 4.7 | 4.3 | 4.5 |
| Kenblue | 4.3 | 5.3 | 4.8 |
| Marquis | 4.0 | 4.3 | 4.2 |
| Merion | 5.3 | 1.7 | 3.5 |
| Midnight | 5.3 | 3.7 | 4.5 |
| Monopoly | 3.0 | 6.3 | 4.7 |
| Nassau | 4.7 | 5.3 | 5.0 |
| Ram I | 5.3 | 3.3 | 4.3 |
| South Dakota | 4.7 | 2.7 | 3.7 |
| Touchdown | 5.0 | 3.7 | 4.3 |
| LSD (.05) | 1.7 | 1.7 | 1.2 |

Drought tolerance (recovery) Rating 1-9; 9 = complete recovery

[a]Pooled data from Halsey, Hubbard and Gervais, Oregon.

TABLE 23

Comparison of Seed Yields in Pounds Per Acre from Solid Row Trials of Ba 73-366 and Other Kentucky Bluegrass Varieties at Gervais, Oregon

| Variety | Lbs/Acre |
|---|---|
| Ba 73-366 | 1382 |
| Bristol | 862 |
| Victa | 1342 |
| LSD (.05) | 216 |

TABLE 24

Comparison of Seed Yields in Pounds Per Acre for Ba 73-366 and Other Kentucky Bluegrass Varieties Over a Two Year Period at Gervais, Oregon

| Variety | Lbs./Acre Year 1 | Lbs./Acre Year 2 |
|---|---|---|
| Ba 73-366 | 920 | 1258 |
| Abbey | 1124 | 1314 |
| Apart | 1244 | 851 |
| Coventry | 786 | 914 |
| Garfield | 1138 | 952 |
| Newport | 1165 | 1002 |
| LSD .05 | 209 | 176 |

TABLE 25

Comparison of Seed Yields in Pounds Per Acre for Ba 73-366 and Other Kentucky Bluegrass Varieties at La Grande, Oregon

| Selection | Lbs./Acre |
|---|---|
| Ba 73-366 | 1,612 |
| Abbey | 1,549 |

TABLE 25-continued

Comparison of Seed Yields in Pounds Per Acre for Ba 73-366 and Other Kentucky Bluegrass Varieties at La Grande, Oregon

| Selection | Lbs./Acre |
|---|---|
| Coventry | 1,046 |
| LSD .05 | 160 |

We claim:

1. A variety of Kentucky bluegrass, substantially as shown and described, characterized by a medium to high level of resistance to several serious diseases, including leaf spot and melting out disease, several rust diseases and dollar spot; a desirable green color throughout the growing season; good drought recovery capability; a medium to high quality dense presistent turf forming ability under a wide variety of environmental conditions; and a high level of seed yielding capacity.

* * * * *

UNITED STATES PATENT AND TRADEMARK OFFICE

CERTIFICATE OF CORRECTION

PATENT NO. : PP-9,036

DATED : January 3, 1995

INVENTOR(S) : Virgil D. Meier et al.

It is certified that error appears in the above—identified patent and that said Letters Patent is hereby corrected as shown below:

Column 1, line 26, change "progency" to --progeny--.
Column 2, line 5, change "Dreschslera" to --Drechslera--.
Column 3, line 26, change "88.88" to --88.8--.

Signed and Sealed this

Eighteenth Day of June, 1996

Bruce Lehman

*Attest:*

BRUCE LEHMAN

*Attesting Officer*

*Commissioner of Patents and Trademarks*